United States Patent [19]
Lantzsch

[11] Patent Number: 5,852,194
[45] Date of Patent: Dec. 22, 1998

[54] N-SUBSTITUTED CIS-N-PROPENYL-ACETAMIDES, AND PROCESS FOR THEIR PREPARATION

[75] Inventor: Reinhard Lantzsch, Wuppertal, Germany

[73] Assignee: Bayer Aktiengesellschaft, Leverkusen, Germany

[21] Appl. No.: 660,433

[22] Filed: Jun. 7, 1996

[30] Foreign Application Priority Data

Jun. 14, 1995 [DE] Germany .................. 195 21 588.5

[51] Int. Cl.$^6$ .................................. C07D 213/08
[52] U.S. Cl. .................. 546/250; 546/345; 564/215; 564/217; 564/219
[58] Field of Search .................. 546/250, 345; 564/215, 217, 219

[56] References Cited

U.S. PATENT DOCUMENTS

5,304,651  4/1994  Lantzsch .................. 546/250

FOREIGN PATENT DOCUMENTS

| 0 546 418 A1 | 6/1993 | European Pat. Off. . |
| 0 670 302 A1 | 9/1995 | European Pat. Off. . |
| 0 701 998 A1 | 3/1996 | European Pat. Off. . |
| 23 34 632 A1 | 1/1975 | Germany . |

OTHER PUBLICATIONS

March, J., Advanced Organic Chemistry, 4th ed., Wiley and Sons, Inc., pp. 581–582.

T. Murai et al., J.Chem.Soc.,Chem.Commun.,*Rhodium(II) Acetate Catalysed Hyrosilylation of Enamides an N–vinylureas leading to 1–(Trialkylsily)alkylamine Derivatives*, pp.2143–2144,(1994).

K.Ng et al.,J.Org.Chem.,vol. 46,No. 14,*Synthesis of Enamides and Amides by Hydrozirconation–Acylation o Schiff Bases*, pp. 2899–2901, (1981).

J.Stille et al,J.Org.Chem.,vol. 45, No. 11,*Isomerization of N–Allylamides and –imides to Aliphatic Enamides by Iron, Rhodium, and Ruthenium Complexes*, pp. 2139–2145, (1980).

A. Hubert et al., J.C.S. Perkin II, *Catalysed Prototropic Rearrangements. . .*, pp.1954–1957, (1973).

O. Meth–Cohn, J. Chem. Soc. Perkins Trans I, *A Versatile New synthesis of Quinolines and Related Fuse Pyridines. . .*, pp. 1173–1182, (1984).

S. Ozaki et al., J.Chem.Soc. Perkins Trans I, *Indirect Electroreductive Cyclisation of N–Allylic. . .* , pp. 2339–2344, (1993).

Primary Examiner—John Kight
Assistant Examiner—Garth M. Dahlen
Attorney, Agent, or Firm—Sprung Kramer Schaefer & Briscoe

[57] ABSTRACT

The present invention relates to new N-substituted cis-N-propenyl-acetamides of the general formula (I)

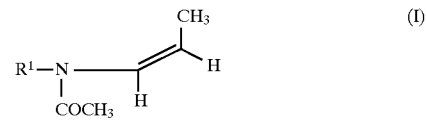

in which $R^1$ represents in each case optionally substituted alkyl, -C(alkyl)$_2$-alkenyl, alkynyl, cycloalkyl, cycloalkylalkyl, aralkyl or hetarylalkyl;

a process for their preparation, and their use for the preparation of 2-chloro-5-methyl-pyridine.

14 Claims, No Drawings

N-SUBSTITUTED CIS-N-PROPENYL-ACETAMIDES, AND PROCESS FOR THEIR PREPARATION

The invention relates to new N-substituted cis-N-propenyl-acetamides, which can be used as intermediates for the preparation of agrochemically active compounds, and to a process for their preparation.

It has already been disclosed that N-alkenyl-acetamides of the formula (A) are obtained when imines of the formula (B) are reacted with acetic anhydride or acetyl chloride in accordance with the following equation, if appropriate in the presence of an acid acceptor:

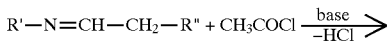

(B)

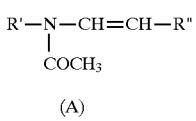

(A)

(cf J. Chem. Soc. Perkin Trans. I 1984, 1173–82 and EP-A 0 546 418)

However, this gives the corresponding trans derivatives; the preparation of cis derivatives has not yet been described.

The present invention relates to 1) new N-substituted cis-N-propenyl-acetamides of the general formula (I)

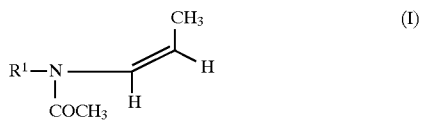

in which $R^1$ represents in each case optionally substituted alkyl, -C(alkyl)$_2$-alkenyl, alkynyl, cycloalkyl, cycloalkylalkyl, aralkyl or hetarylalkyl;

2) a process for the preparation of N-substituted cis-N-propenyl-acetamides of the general formula (I)

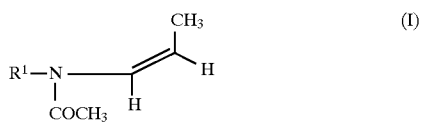

in which $R^1$ represents in each case optionally substituted alkyl, -C(alkyl)$_2$-alkenyl, alkynyl, cycloalkyl, cycloalkylalkyl, aralkyl or hetarylalkyl, characterized in that acetamides of the general formula (II)

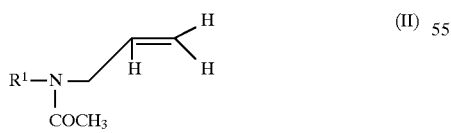

in which $R^1$ has the abovementioned meaning are isomerized using strong bases, if appropriate in the presence of a diluent;

and 3) the use of the N-substituted cis-N-propenyl-acetamides of the general formula (I) for the preparation of 2-chloro-5-methyl-pyridine, of the formula (IV)

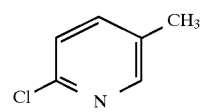

by reaction by means of "Vilsmeier reagent", i.e. with a formamide derivative of the general formula (II)

in which $R^2$ and $R^3$ are identical or different and represent alkyl or cycloalkyl, or together represent alkanediyl, and with a chlorinating agent at temperatures between 20° and 150° C., if appropriate in the presence of a diluent.

Surprisingly, the new N-substituted cis-N-propenyl-acetamides of the formula (I) can be obtained by the process according to the invention in a simple manner and in very good yields, even though similar isomerization processes have been described hitherto as photochemical reactions using iron carbonyls as rearrangement catalysts (cf., for example, J. Chem. Soc. Perkin Trans II, 1973, pp. 1954–57). The process according to the invention is thus especially suitable for a preparation on an industrial scale, which represents a valuable enrichment of the prior art.

N-substituted cis-N-propenyl-acetamides of the formula (I) are used for the preparation of 2-chloro-5-methylpyridine.

Compounds of the formula (I) (which are preferably prepared by the process according to the invention are those in which $R^1$ represents $C_1$–$C_6$-alkyl which is optionally substituted by $C_1$–$C_1$-alkoxy;

or represents 1-buten-4-yl, 2-buten-4-yl; propynyl or butynyl;

or represents cyclopropyl, cyclobutyl, cyclopentyl, cyclohexyl, cyclopropylmethyl, cyclobutylmethyl, cyclopentylmethyl or cyclohexylmethyl, or represents benzyl, phenylethyl, phenylpropyl, naphthylmethyl, thienylmethyl or pyridylmethyl, each of which is optionally monosubstituted to trisubstituted by identical or different substituents, substituents which may be mentioned in each case being: halogen, $C_1$–$C_4$-alkyl and $C_1$–$C_4$-alkoxy.

Compounds of the formula (I) which are, in particular, prepared by the process according to the invention are those in which $R^1$ represents methyl, ethyl, n- or i-propyl and n-, iso-, sec- or t-butyl, each of which is optionally substituted by methoxy or ethoxy;

or represents benzyl or phenethyl, each of which is optionally monosubstituted to disubstituted by identical or different substituents, substituents which may be mentioned being: fluorine, chlorine, bromine, methyl, ethyl, n- or iso-propyl, n-, iso-, sec- or t-butyl, methoxy and ethoxy;

or represent cyclohexyl or chloropyridylmethyl.

The abovementioned definitions of radicals, in general terms or in preferred ranges, apply to the end products of the formula (I) and, analogously, to the starting materials required for the preparation.

If, for example, N-methyl-N-allylacetamide is used as starting material and potassium hydroxide as the base, the course of the reaction of the process according to the invention can be represented by the following equation:

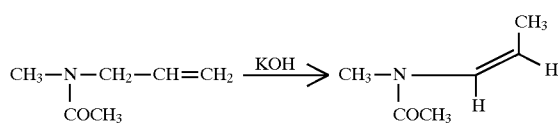

Formula (II) provides a general definition of the acetamides to be used as starting materials in the process according to the invention for the preparation of the compounds of the formula (I). In formula (II), $R^1$ preferably, or in particular, has those meanings which have already been mentioned above in connection with the description of the new compounds of the formula (I) as being preferred, or particularly preferred, for $R^1$.

The acetamides of the formula (II) are known and/or can be prepared by processes known per se (cf., for example, DE-OS (German Published Specification) 23 34 632 or J. Chem. Soc. Perkin Trans. I 1993, 2344).

The isomerization according to the invention is carried out in the presence of strong bases. These include, for example, alkali metal hydroxides, such as lithium hydroxide, sodium hydroxide or potassium hydroxide, and also alkali metal alcoholates, such as sodium methylalte, sodium ethylate, sodium isopropylate, sodium n-butylate, sodium sec-butylate, sodium tert-butylate, potassium n-butylate, potassium sec-butylate or potassium tert-butylate.

If appropriate, the isomerization according to the invention is carried out in the presence of a diluent. Suitable diluents are inert, preferably aprotic, polar solvents. These include, in particular, ethers, such as methyl tert-butyl ether, methyl tert-amyl ether, 1,2-dimethoxoxyethane; diethoxymethane, ethylene glycol dimethyl ether or ethylene glycol diethyl ether, furthermore nitriles, such as acetonitrile, propionitrile, benzonitrile or butyronitrile, furthermore amides, such as formamide, dimethylformamide, dimethylformamide, di-cyclohexylformamide, dibutylformamide, acetamide, dimethyl acetamide, N-methyl-pyrrolidone, N-methyl-E-caprolactam, ureas, such as tetramethylurea, sulphoxides and sulphones, such as dimethyl sulphoxide or sulpholane.

When carrying out the isomerization according to the invention, the reaction temperatures can be varied within a substantial range. In general, the process is carried out at temperatures between −20° and +150° C., preferably at temperatures between 0° C. and 100° C., depending on the base used and/or the solvent which has optionally been used, to achieve a sufficiently high reaction rate.

To carry out the isomerization according to the invention, between 0.01 and 2 mol, in particular between 0.05 and 1 mol, of base are generally employed per mol of acetamide of the formula (II).

Working-up can be carried out in the customary manner using water. After neutralization of the base, the mixture is extracted using a suitable solvent. The compounds can be purified by distillation. If catalytic amounts of base and no solvent or a solvent which is suitable for the next step are used, the compounds can also be directly reacted further without isolation and purification to give 2-chloro-5-methyl-pyridine, of the formula (IV).

The N-substituted cis-N-propenyl-acetamides of the formula (I) which can be prepared by the isomerization according to the invention can be reacted to give 2-chloro-5-methyl-pyridine, of the formula (IV), by reaction with a formamide derivative of the formula (III) and with a chlorinating agent.

2-Chloro-5-methyl-pyridine, which can thus be prepared, can be used as intermediate for insecticides (cf., for example, EP-A 0 163 855).

Surprisingly, 2-chloro-5-methylpyridine can be obtained by this route in a simple manner and in good yields, even though the steric arrangement of the substituents in the N-substituted cis-N-propenyl-acetamides of the formula (I) seems unsuitable for pyridine cyclization:

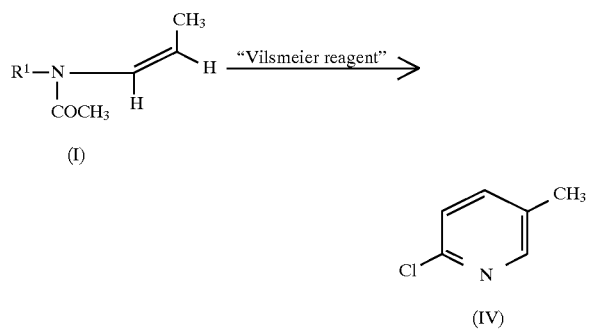

Formula (III) provides a general definition of the formamide derivatives furthermore to be used as starting materials for the preparation of 2-chloro-5-methyl-pyridine, of the formula (IV). In the formula (III), $R^2$ and $R^3$ are identical or different and preferably represent straight-chain or branched alkyl having 1 to 6 carbon atoms, such as, in particular, methyl, ethyl, n- or i-propyl or n-, iso-, sec- or t-butyl; furthermore represents cycloalkyl having 3 to 6 carbon atoms, such as, in particular, cyclopentyl or cyclohexyl; and together represent alkanediyl having 2 to 6 carbon atoms, such as, in particular, butane-1,4-diyl or pentane-1,5-diyl.

Examples of the formamide derivatives of the formula (III) which may be mentioned are: N,N-dimethyl-formamide, N,N-diethyl-formamide, N,N-dipropyl-formamide, N,N-dibutyl-formamide, N-cyclohexyl-N-methyl-formamide, N,N-dicyclohexyl-formamide.

The formamide derivatives of the formula (III) are known chemicals for organic synthesis.

The process for the preparation of 2-chloro-5-methyl-pyridine, of the formula (IV), is carried out using a chlorinating agent. The customary chlorinating agents can be used for this purpose, for example phosphoryl chloride (phosphorus oxychloride), phosphorus(V) chloride, phosgene, oxalyl chloride, thionyl chloride, perchlorobutanoyl chloride, dichlorobenzodioxol, N,N-dimethyl-chloromethylimmonium chloride or N,N-diethyl-chloromethylimmonium chloride.

Suitable diluents for carrying out the process for the preparation of 2-chloro-5-methyl-pyridine, of the formula (IV), are the customary organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, tetrachloromethane; ethers, such as diethyl ether, diisopropyl ether, dioxane, tetrahydrofuran or ethylene glycol dimethyl ether or ethylene glycol diethyl ether; nitriles, such as acetonitrile, propionitrile or butyronitrile; amides, such as N,N-dimethylformamide, N,Ndimethylacetamide, N-methylformanilide, N-methyl-pyrrolidone or hexamethylphosphoric triamide; sulphoxides, such as dimethyl sulphoxide, and sulphones, such as tetramethylene sulphone.

When carrying out the process for the preparation of 2-chloro-5-methyl-pyridine, of the formula (IV), the reaction temperatures can be varied within a substantial range. In general, the process is carried out at temperatures between −30° C. and +150° C., preferably at temperatures between −10° C. and +120° C., the starting phase preferably being carried out between −10° C. and +40° C. and the subsequent phase between +20° C. and 120° C. However, it is also possible to carry out the process directly at elevated temperature and to produce the "Vilsmeier reagent" in situ.

The process is generally carried out under atmospheric pressure. However, it is also possible to carry out the process under elevated or reduced pressure, in general between 0.1 bar and 10 bar.

To carry out the process for the preparation of 2-chloro-5-methyl-pyridine, of the formula (IV), between 1 and 10 mol, preferably between 1.5 to 5.0 mol, in particular between 2.0 and 4.0 mol, of chlorinating agent and between 1 and 10 mol, preferably between 2.0 and 4.0 mol, of formamide derivative of the formula (III) are generally employed per mol of N-substituted cis-N-propenyl-acetamide of the formula (I).

Working-up can be carried out in the customary manner.

PREPARATION EXAMPLES

Example 1

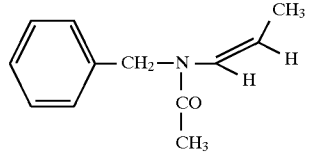

(Base: potassium tert-butylate; solvent: 1.2-dimethoxiethane)

9.47 g (0.05 mol) of N-benzyl-N-allylacetamide are dissolved in 50 ml of dry 1,2-dimethoxethane. 5.6 g (0.05 mol) of potassium tert-butylate are added under protective gas at 20° C. The reaction is exothermic, and the colour of the solution turns dark red. The mixture is heated with stirring for one hour at 40° C., ice-water is added, and the pH is brought to 7. After the mixture has been extracted three times with methylene chloride, the combined organic phases are dried and concentrated.

9.3 g of a red oil, which is purified by bulb tube distillation (jacket temperature 150° C., 0.5 mbar), are obtained.

8.3 g (87.6% of theory) of cis-N-benzyl-N-propenyl-acetamide of refractive index=1.535 are obtained.

$^1$H NMR (CDCl$_3$, d in ppm): 1.42–1.45 (dd, CH$_3$), 2.05 (s, CH$_3$), 4.63 (s, CH$_2$), 5.47–5.52 (m, CH), 5.97–6.00 (dd, CH), ~7.3 (m, 5H).

(Base: potassium hydroxide, solvent: dimethyl sulphoxide)

9.47 g (0.05 mol of N-benzyl-N-allylacetamide are dissolved in 30 ml of dimethyl sulphoxide, and 0.28 g (0.005 mol) of potassium hydroxide are added. The mixture is stirred at room temperature for 24 hours, most of the solvent is distilled off in vacuo, ice-water is added, and the pH is brought to neutral. Working-up is carried out as above. 9.1 g are obtained (without distillation); content: 91.3%. This corresponds to a yield of 87.7% of theory.

(Base: potassium hydroxide: solvent: none)

9.47 g (0.05 mol) of N-benzyl-N-allylacetamide and 0.66 g (0.01 mol) of potassium hydroxide powder (85%) are heated for one hour at 80° C. with stirring in the absence of a solvent. The mixture is cooled, ice-water is added, and the pH is brought to 8 using dilute hydrochloric acid, and the mixture is extracted three times using methylene chloride. The organic phases are combined and dried, and the solvent is distilled off under reduced pressure (rotary evaporator).

9.1 g of an orange oil which has a N-benzyl-N-cis-propenyl-acetamide content of 87.5% (GC) and which, if required, can be purified further by distillation, are obtained.

Other examples of the compounds of the formula (I) which can be obtained analogously to Example 1 and following the general preparation instructions are those listed in the table below:

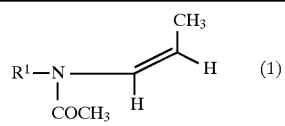

| Example No. | R$^1$ | Physical constant |
|---|---|---|
| 2 | CH$_3$ | N$_D^{20}$ = 1.462 |
| 3 | n-C$_4$H$_9$ | N$_D^{20}$ = 1.470 |
| 4 | t-C$_4$H$_9$ | N$_D^{20}$ = 1.465 |
| 5 | CH$_3$OCH$_2$CH$_2$— | N$_D^{20}$ = 1.471 |
| 6 | 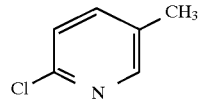 | N$_D^{20}$ = 1.487 |
| 7 | 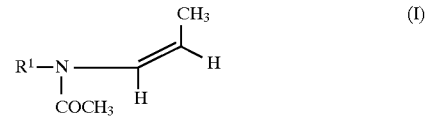 | N$_D^{20}$ = 1.561 |

Preparation of 2-chloro-5-methyl-pyridine (IV)

10.4 g (content: 91.3%, 0.05 mol) of cis-N-benzyl-N-propenyl-acetamide are dissolved in 25 ml of acetonitrile. 11 g (0.15 mol) of dimethylformamide are then added, and 19 g (0.15 mol) of oxalyl chloride are subsequently added dropwise at 20°–25° C., with cooling. The mixture is subsequently refluxed for 18 hours and cooled, and the solvent is distilled off in vacuo. The reaction product is stirred with ice-water and extracted three times using methylene chloride. The organic phases are combined, dried and concentrated.

11.8 g of a clear fluid are obtained; the 2-chloro-5-methyl-pyridine, which can be purified by distillation, amounts to 47%. Yield: 86.9% of theory.

I claim:

1. N-substituted cis-N-propenyl-acetamides of the formula (I)

$$R^1-N(COCH_3)-CH=CH-CH_3 \quad (I)$$

in which

R$^1$ represents in each case optionally substituted alkyl, -C(alkyl)$_2$-alkenyl, alkynyl, cycloalkyl, cycloalkyalkyl, aralkyl or hetarylalkyl, wherein the N-substituted cis-N-propenyl-acetamides are essentially free of the trans isomers.

2. Process for the preparation of N-substituted cis-N-propenyl-acetamides of the formula (I)

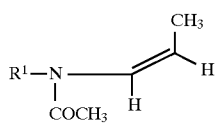

in which
R¹ represents in each case optionally substituted alkyl, -C(alkyl)₂-alkenyl, alkynyl, cycloalkyl, cycloalkyalkyl, aralkyl or hetarylalkyl,
wherein acetamides of the formula (II)

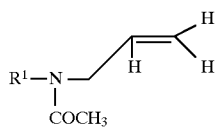

in which
R¹ has the abovementioned meaning
are isomerized using strong bases in the presence of an aprotic polar diluent or in the absence of a diluent.

3. A method for the preparation of 2-chloro-5-methyl-pyridine, of the formula (IV)

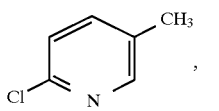

by reaction of an N-substituted cis-N-propenyl-acetamide of the formula

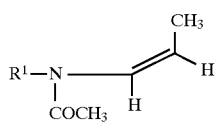

in which
R¹ represents in each case optionally substituted alkyl, -C(alkyl)₂-alkenyl, alkinyl, cycloalkyl, cycloalkylalkyl, aralkyl or hetarylalkyl
with a formamide derivative of the formula (III)

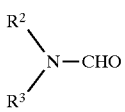

in which
R² and R³ are identical or different and represent alkyl or cycloalkyl, or together represent alkanediyl,
and with a chlorinating agent, at temperatures between 20° and 150° C., if optionally in the presence of a diluent.

4. N-substituted cis-N-propenyl-acetamides of the formula (I)

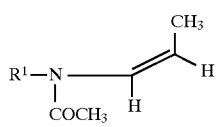

in which
R¹ represents in each case optionally substituted alkyl, -C(alkyl)₂-alkenyl, alkynyl, cycloalkyl, cycloalkyalkyl, aralkyl or hetarylalkyl, wherein the N-substituted cis-N-propenyl-acetamides are at least 87.5% free of the trans isomers.

5. Acetamides according to claim 1, wherein
R¹ represents $C_1$–$C_6$-alkyl which is optionally substituted by $C_1$–$C_2$-alkoxy;
or represents 1-buten4-yl, 2-buten-4-yl; propynyl or butynyl;
or represents cyclopropyl, cyclobutyl, cyclopentyl, cyclohexyl, cyclopropylmethyl, cyclobutylmethyl, cyclopentylmethyl or cyclohexylmethyl, or represents
benzyl, phenylethyl, phenylpropyl, naphthylmethyl, thienylmethyl or pyridylmethyl, each of which is optionally monosubstituted to trisubstituted by identical or different substituents, said substituents being halogen, $C_1$–$C_4$-alkyl and $C_1$–$C_4$-alkoxy.

6. Process according to claim 2, wherein
R¹ represents $C_1$–$C_6$-alkyl which is optionally substituted by $C_1$–$C_2$-alkoxy;
or represents 1-buten4-yl, 2-buten4-yl; propynyl or butynyl;
or represents cyclopropyl, cyclobutyl, cyclopentyl, cyclohexyl, cyclopropylmethyl, cyclobutylmethyl, cyclopentylmethyl or cyclohexylmethyl, or represents
benzyl, phenylethyl, phenylpropyl, naphthylmethyl, thienylmethyl or pyridylmethyl, each of which is optionally monosubstituted to trisubstituted by identical or different substituents, said substituents being halogen, $C_1$–$C_4$-alkyl and $C_1$–$C_4$-alkoxy.

7. Method according to claim 3, wherein
R¹ represents $C_1$–$C_6$-alkyl which is optionally substituted by $C_1$–$C_2$-alkoxy;
or represents 1-buten-4-yl, 2-buten4-yl; propynyl or butynyl;
or represents cyclopropyl, cyclobutyl, cyclopentyl, cyclohexyl, cyclopropylmethyl, cyclobutylmethyl, cyclopentylmethyl or cyclohexylmethyl, or represents
benzyl, phenylethyl, phenylpropyl, naphthylmethyl, thienylmethyl or pyridylmethyl, each of which is optionally monosubstituted to trisubstituted by identical or different substituents, said substituents being halogen, $C_1$–$C_4$-alkyl and $C_1$–$C_4$-alkoxy.

8. Acetamides according to claim 4, wherein
R¹ represents $C_1$–$C_6$-alkyl which is optionally substituted by $C_1$–$C_2$-alkoxy;
or represents 1-buten-4-yl, 2-buten-4-yl; propynyl or butynyl;
or represents cyclopropyl, cyclobutyl, cyclopentyl, cyclohexyl, cyclopropylmethyl, cyclobutylmethyl, cyclopentylmethyl or cyclohexylmethyl, or represents
benzyl, phenylethyl, phenylpropyl, naphthylmethyl, thienylmethyl or pyridylmethyl, each of which is optionally monosubstituted to trisubstituted by identical or different substituents, said substituents being halogen, $C_1$–$C_4$-alkyl and $C_1$–$C_4$-alkoxy.

9. Acetamides according to claim 1, wherein
R¹ represents methyl, ethyl, n- or iso-propyl and n-, iso-, sec-, or t-butyl, each of which is optionally substituted by methoxy or ethoxy;
or represents benzyl or phenethyl, each of which is optionally monosubstituted to disubstituted by identical or different substituents, said substituents being fluorine, chlorine, bromine, methyl, ethyl, n- or iso-propyl, n-, iso-, sec-, or t-butyl, methoxy and ethoxy;

or represent cyclohexyl or chloropyridylmethyl.

10. Process according to claim 2, wherein $R^1$ represents methyl, ethyl, n- or i-propyl and iso-propyl and n-, iso-, sec-, or t-butyl, each of which is optionally substituted by methoxy or ethoxy; or represents benzyl or phenethyl, each of which is optionally monosubstituted to disubstituted by identical or different substituents, said substituents being fluorine, chlorine, bromine, methyl, ethyl, n- or iso-propyl, n-, iso-, sec-, or t-butyl, methoxy and ethoxy;

or represent cyclohexyl or chloropyridylmethyl.

11. Method according to claim 3, wherein $R^1$ represents methyl, ethyl, n- or iso-propyl and n-, iso-, sec-, or t-butyl, each of which is optionally substituted by methoxy or ethoxy;

or represents benzyl or phenethyl, each of which is optionally monosubstituted to disubstituted by identical or different substituents, said substituents being fluorine, chlorine, bromine, methyl, ethyl, n- or i-propyl, n-, i-, s- or t-butyl, methoxy and ethoxy;

or represent cyclohexyl or chloropyridylmethyl.

12. Acetamides according to claim 4, wherein $R^1$ represents methyl, ethyl, n- or iso-propyl, n-, iso-, sec-, or t-butyl, each of which is optionally substituted by methoxy or ethoxy;

or represents benzyl or phenethyl, each of which is optionally monosubstituted to disubstituted by identical or different substituents, said substituents being fluorine, chlorine, bromine, methyl, ethyl, n- or iso-propyl, n-, iso-, sec-, or t-butyl, methoxy and ethoxy;

or represent cyclohexyl or chloropyridylmethyl.

13. Method according to claim 2, wherein the diluent is at least one selected from the group consisting of ethers, nitriles, amides, pyrrolidones, lactams, ureas, sulfoxides and sulfones.

14. Method according to claim 2, wherein the diluent is at least one selected from the group consisting of methyl tert-butyl ether, methyl tert-amyl ether, 1,2-dimethoxyethane, diethoxymethane, ethylene glycol dimethyl ether, ethylene glycol diethyl ether, acetonitrile propionitrile, benzonitrile, butyronitrile, formamide, dimethylformamide, diethylformamide, di-cyclohexylformamide, dibutylformamide, acetamide, dimethyl acetamide, N-methyl-pyrrolidone, N- methyl-E-caprolactam, tetramethylurea, dimethyl sulfoxide and sulfolane.

* * * * *